US012637650B2

(12) United States Patent
Sustarich et al.

(10) Patent No.: US 12,637,650 B2
(45) Date of Patent: May 26, 2026

(54) APPARATUS AND METHODS FOR INCREASED TRANSFORMATION EFFICIENCY FOR ELECTROPORATION OF MICROORGANISMS

(71) Applicant: National Technology & Engineering Solutions of Sandia, LLC, Albuquerque, NM (US)

(72) Inventors: Jess Sustarich, San Francisco, CA (US); Anup K. Singh, Danville, CA (US); Lauren Washburn, Albuquerque, NM (US); William Gaillard, Walnut Creek, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 859 days.

(21) Appl. No.: 17/877,043

(22) Filed: Jul. 29, 2022

(65) Prior Publication Data

US 2023/0036493 A1     Feb. 2, 2023

Related U.S. Application Data

(60) Provisional application No. 63/227,927, filed on Jul. 30, 2021.

(51) Int. Cl.
*C12M 1/42*        (2006.01)
*C12N 13/00*       (2006.01)
*G01N 15/14*       (2024.01)

(52) U.S. Cl.
CPC ............. *C12M 35/02* (2013.01); *C12N 13/00* (2013.01); *G01N 15/1468* (2013.01)

(58) Field of Classification Search
CPC ...... C12M 35/02; C12M 23/12; C12M 13/00;

C12M 25/02; C12N 13/00; C12N 15/87; C12N 15/8207; C12N 15/8206; G01N 15/1468; G01N 33/48728; A61N 1/327; A61N 1/306; A61K 48/00; A61K 38/00; H03K 3/57
See application file for complete search history.

(56) References Cited

U.S. PATENT DOCUMENTS

| | | | | |
|---|---|---|---|---|
| 2002/0064841 A1* | 5/2002 | Klemic | ............ | G01N 33/48728 435/164 |
| 2005/0164191 A1* | 7/2005 | Branden | ................ | C40B 50/08 435/7.1 |
| 2019/0383770 A1* | 12/2019 | Choi | ........................ | C12Q 1/68 |

* cited by examiner

*Primary Examiner* — Michael L Hobbs
(74) *Attorney, Agent, or Firm* — Kilpatrick Townsend & Stockton LLP

(57)                ABSTRACT

The present disclosure relates to a high throughput, scalable system for electroporation of biological cells. The two part system comprises an electroporation reaction array that interfaces with a control unit, providing electrical pulse, temperature control, and mixing of the sample contents. The control unit automates the entire process; electroporation, cell recovery and outgrowth are performed in a electroporation array assembly. The bottom of each reaction well of the electroporation array assembly contains a pair of coplanar electrodes. The bottom surface containing the electrodes is treated in a way to render it hydrophilic. This results in increased wetting of the electrodes thereby increasing transformation efficiency. The electrode configuration allows for processing of smaller sample volumes, reducing the consumption of expensive biological reagents by several orders of magnitude compared to conventional cuvette-based electroporation devices.

19 Claims, 12 Drawing Sheets

150

145

155    160

130    135

400

405

435 425

500

505

APPARATUS AND METHODS FOR INCREASED TRANSFORMATION EFFICIENCY FOR ELECTROPORATION OF MICROORGANISMS

CROSS-REFERENCE TO RELATED APPLICATION

This application claims the benefit of U.S. Provisional Application No. 63/227,927, filed Jul. 30, 2021, the entire contents of which is hereby incorporated for all purposes in its entirety.

STATEMENT OF GOVERNMENT SUPPORT

The invention was made with government support under Contract Nos. DE-AC02-05CH11231 awarded by the U.S. Department of Energy. The government has certain rights in the invention

FIELD OF THE INVENTION

The present disclosure relates to electroporation of biological cells, and in particular to a scalable system for electroporation, increasing the throughput and efficiency of synthetic biology, genetic engineering and genome editing for the purposes of biomanufacturing and bioengineering.

BACKGROUND

The application of electric field waveforms has an innumerable number of uses for the manipulation and analysis of biologic samples; manipulation of particle or fluid flow as in electrophoresis, dielectrophoresis, electroosmosis and electrowetting, detection of species or a reaction by measuring conductivity, impedance or electrochemical potential, or delivery of molecules into biological cells by electroporation.

Electroporation is a widely-used method for permeabilization of cell membranes by temporary generation of membrane pores with electrical stimulation. The applications of electroporation include the delivery of DNA, RNA, siRNA, non-naturally occurring oligonucleotides, peptides, proteins, antibodies, drugs or other substances to a variety of cells such as mammalian cells, plant cells, yeasts, other eukaryotic cells, bacteria, other microorganisms, and even cells within human patients. Electrical stimulation may also be used for cell fusion in the production of hybridomas or other fused cells. Electrical cell fusion may be regarded as a special form of electroporation.

Electroporation can be used for both transient and stable transfection of mammalian cells. Cells are placed in suspension in an appropriate electroporation buffer and put into the wells of the device. DNA is added and the cells are subjected to a high-voltage electrical pulse of defined magnitude and length. The cells are then allowed to recover briefly before they are placed in normal (non-selecting) cell growth medium.

With the advent of molecular cloning, the process of transformation was exploited to introduce recombinant plasmid DNA into bacterial strains that were made "competent," or more permeable, for DNA uptake. Electroporation involves exposing competent cells and DNA to a brief pulse of a high-voltage electric field. This treatment is believed to induce transient pores in cell membranes, which permit DNA entry into the cells. The most common type of electric pulse in bacterial transformation is exponential decay, where a set voltage is applied and allowed to decay over a few milliseconds. Following electroporation, transformed cells are cultured in antibiotic-free liquid medium for a short period to allow expression of antibiotic resistance gene(s) from the acquired plasmid to begin. This step improves cell viability and cloning efficiency.

Screening for loss-of-function phenotypes typically requires the knockout or knockdown of an endogenous gene or protein. This can be achieved by transfection of short interfering (si) RNA oligonucleotides or short hairpin (sh) RNA-based plasmid vectors. RNAi has emerged as a powerful tool for loss-of-function screening, not least because siRNA libraries are commercially available in several customizable formats and sizes. Genome-wide screens using siRNA libraries have provided valuable insights into cellular factors required for virus infection, endocytosis, and regulation of mitosis, just to name a few. Both siRNA and shRNA use double-stranded RNA molecules that lead to sequence-specific degradation of mRNA in the target cells. Efficient delivery of the siRNA or shRNA to the cytoplasm is a prerequisite for efficient knockdown of the target gene. A common siRNA or shRNA delivery method is electroporation.

CRISPR/Cas9 is an effective and easy-to-use tool for editing the genome of many human cancer cell lines. However, in some hard-to-transfect cell lines and primary cells, gene editing is more challenging. Electroporation works very efficiently in numerous cell lines and primary cells that are difficult to transfect by conventional chemical-based transfection methods.

BRIEF SUMMARY

In various embodiments, an electroporation array assembly comprises: a polymer housing forming side walls of reaction wells; and an electrode array layer bonded to a bottom surface of the polymer housing, where: the electrode array layer forms a bottom surface of the reaction wells, the electrode array layer comprises: (i) a substrate, and (ii) an array of electrodes formed on the substrate, the array of electrodes is arranged such that a pair of electrodes is disposed in each of the reaction wells, each pair of electrodes are coplanar with an interdigitated configuration or geometry, and the substrate, the array of electrodes, or the combination thereof are hydrophilic.

In some embodiments, the substrate, the array of electrodes, or the combination thereof are hydrophilic with a water contact angle of less than 40 degrees.

In some embodiments, each pair of electrodes comprise a ground electrode adjacent to a corresponding active electrode, each pair of electrodes protrude from or are raised above a top surface of the substrate, and microchannels are formed between the ground electrode and the active electrode of each pair of electrodes.

In some embodiments, each electrode of the array of electrodes is comprised of conductive traces, which are formed on the substrate in the interdigitated configuration or geometry.

In some embodiments, the side walls of the reaction wells are hydrophobic with a water contact angle of greater than 80 degrees.

In some embodiments, an electrical connection is routed from each pair of electrodes through the substrate to contacts on a bottom surface of the electrode array layer.

In some embodiments, the electrical connection is a wiring layer comprised of conductive traces and the conductive traces are arranged in a circuit architecture that includes isolated connections using multiple addressable signal lines and/or signal lines with switches that enable each pair of electrodes to be individually addressable.

In various embodiments, an electroporation system comprises: an electroporation array assembly comprising: a housing forming side walls of reaction wells; and an electrode array layer bonded to a bottom surface of the housing, where: the electrode array layer forms a bottom surface of the reaction wells, the electrode array layer comprises: (i) a substrate, and (ii) an array of electrodes formed on the substrate, the substrate, the array of electrodes, or the combination thereof are hydrophilic, and an electrical connection is routed from each electrode of the array of electrodes through the substrate to a first set of contacts on a bottom surface of the electrode array layer; and a control unit comprising: a temperature controlled pad, a second set of contacts located on the periphery of the temperature controlled pad and arranged to align with and make electrical contact with the first set of contacts of the electroporation array assembly, and a microcontroller electrically connected to the second set of contacts and configured to deliver a voltage waveform to the array of electrodes via the first set of contacts and the second set of contacts.

In some embodiments, the temperature controlled pad is in direct contact with the bottom surface of the electrode array layer.

In some embodiments, the array of electrodes is arranged such that a pair of electrodes is disposed in each of the reaction wells, and each pair of electrodes are coplanar with an interdigitated configuration or geometry.

In some embodiments, the electrical connection is a wiring layer comprised of conductive traces and the conductive traces are arranged in a circuit architecture that includes isolated connections using either multiple addressable signal lines and/or signal lines with switches that enable each pair of electrodes to be individually addressable In some embodiments, the microcontroller is part of a switching board that further comprises multiplexers configured to individually address each pair of electrodes.

In some embodiments, where: each pair of electrodes comprise a ground electrode adjacent to a corresponding active electrode, each pair of electrodes protrude from or are raised above a top surface of the substrate, and microchannels are formed between the ground electrode and the active electrode of each pair of electrodes.

In some embodiments, the substrate, the array of electrodes, or the combination thereof are hydrophilic with a water contact angle of less than 40 degrees.

In some embodiments, each electrode of the array of electrodes is comprised of conductive traces, which are formed on the substrate in the interdigitated configuration or geometry.

In some embodiments, the side walls of the reaction wells are hydrophobic with a water contact angle of greater than 80 degrees.

In various embodiments, a method of electroporation comprises: obtaining a electroporation system comprising: (i) an electroporation array assembly comprising: a housing forming side walls of reaction wells; and an electrode array layer bonded to a bottom surface of the housing, where: the electrode array layer forms a bottom surface of the reaction wells, the electrode array layer comprises: (a) a substrate, and (b) an array of electrodes formed on the substrate, the substrate, the array of electrodes, or the combination thereof are hydrophilic, and an electrical connection is routed from each electrode of the array of electrodes through the substrate to a first set of contacts on a bottom surface of the electrode array layer; and (ii) a control unit comprising: a temperature controlled pad, an agitator, a second set of contacts located on the periphery of the temperature controlled pad and arranged to align with and make electrical contact with the first set of contacts of the electroporation array assembly, and a microcontroller electrically connected to the second set of contacts and configured to deliver a voltage waveform to the array of electrodes via the first set of contacts and the second set of contacts; dispensing a sample into the reactions wells; controlling, using the temperature control pad, a temperature of the sample such that the temperature of the sample is at a first temperature or within a first temperature range; applying, using the microcontroller, the voltage waveform to one or more electrodes of the array of electrodes; and controlling, using the temperature control pad, the temperature of the sample such that the temperature of the sample is at a second temperature or within a second temperature range, where the second temperature and the second temperature range are different from the first temperature and the first temperature range.

In some embodiments, the voltage waveform actuates the one or more electrodes and increase permeability of cells in the sample allowing external substances to be introduced into the cells.

In some embodiments, the array of electrodes is arranged such that a pair of electrodes is disposed in each of the reaction wells, and each pair of electrodes are coplanar with a interdigitated configuration or geometry.

In some embodiments, the method further comprises: adding a buffer into the reactions wells to facilitate growth of the cells; and agitating, using the agitator of the control unit, the buffer and sample in the reaction wells.

BRIEF DESCRIPTION OF THE DRAWINGS

The present invention will be better understood in view of the following non-limiting figures, in which.

DETAILED DESCRIPTION

I. Introduction

Figure 1A:
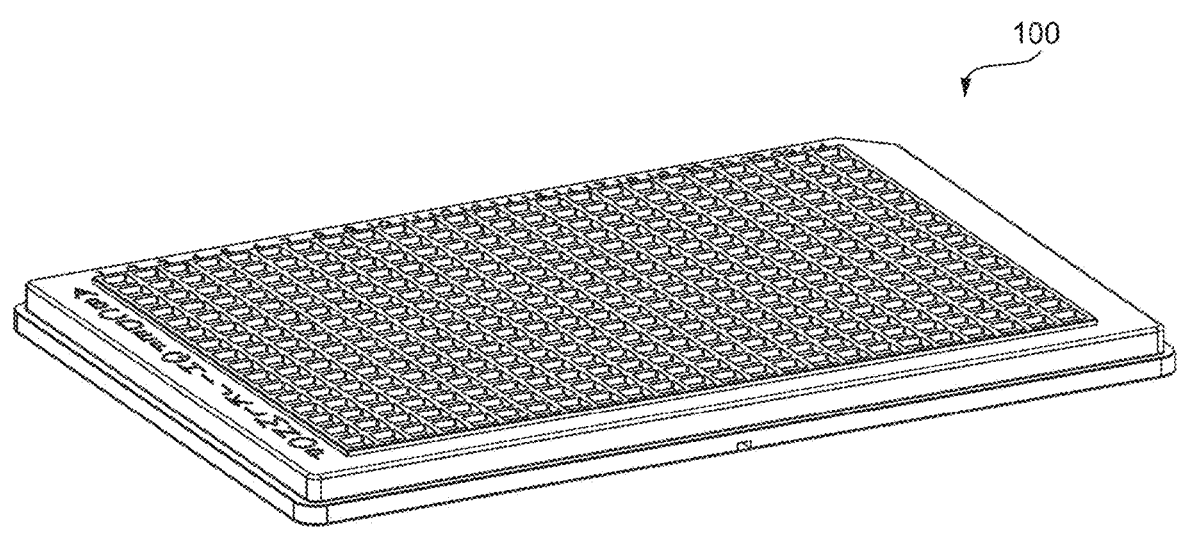
FIGS. 1A-1G show an electroporation array assembly in accordance with various embodiments.

Conventional electroporation devices have parallel-plate electrodes with electrode gaps of at least 1 mm, with protocols requiring volumes on the order of 100 µL. The most common use of electroporation is to transfect a biological cell with DNA of a specified sequence to encode engineered proteins to be built within the cell. The custom tailored DNA is fairly expensive to fabricate, making a reduced sample volume desirable given that a certain threshold DNA concentration must be maintained for a successful transfection it is not sufficient to simply dilute a sample volume in order to reduce the amount of DNA used. Moreover, during the electroporation of biological cells, the sample volume to undergo electroporation is kept at 4° C. to reduce effects of joule heating resulting from the applied voltage waveform. Immediately after the waveform is applied, the biological cells require rapid heating to 37° C. to increase the survival rate of the biological cells.

In view of these challenges and limitations, various embodiments disclosed herein are directed to a two part system and the individual components thereof for high throughput electroporation. The system is comprised of a removable electroporation array assembly, and a control unit providing electrical connectivity and temperature control of the electroporation array assembly contents. The electroporation array assembly is comprised of two layers: an electroporation electrode array layer, bonded to a polymer housing, making up an array of electroporation reaction wells, each containing a pair of electroporation electrodes. The polymer housing may contain an array of through hole vacancies that makeup the side walls of the reaction wells, providing fluidic isolation and structural rigidity. The top side of the electrode array layer supports the electroporation electrodes on an electrically insulating substrate, with electrical connection routes through the insulating substrate to contact pads on the bottom side of the electrode array layer, used to interface with the control unit. The top side of the electroporation electrode array layer makes up the bottom floor area of the assembly's reaction well(s), with the electrodes partially or completely covering its entirety.

The top side of the electrode array layer undergoes a process prior to bonding with the polymer housing, to make it hydrophilic. The two-dimensional (2D) top down design of the electrodes are arranged in a manner to utilize capillary forces afforded by the three-dimensional (3D) structure and hydrophilic treatment of the top side of the electrode array layer, to pull the dispensed aqueous reaction volume from the center of the reaction well floor, spreading it out over the entire surface of the electrodes. This maximizes the contact of the aqueous sample with the surface of the electrodes, allowing for a much higher percentage of the reaction volume to experience the relevant strength of the applied electric field required to perform electroporation. This configuration may be used for reduced reaction volumes. Advantageously, a reduction in operating reaction volume allows for a drastic reduction of reagents and cost per experiment.

Voltage waveforms are sent to the electroporation electrode pairs through the electrical connection provided by the control unit, from an internally or externally housed waveform generator. The circuit architecture of the electrode array enables the electrodes to be individually addressable, allowing different voltage waveforms to be selectively applied to each well individually. Advantageously, this increases the versatility of the system and the scalability of experiments, in order to fine tune parameters that increase the overall transformation efficiency.

The contact pads on the bottom side of the electrode layer may be positioned on the periphery, so that the center area of the bottom side of the electrode array layer is physically uninhibited and available for thermal contact, allowing the corresponding control unit to provide electronic connectivity to the electroporation electrodes while simultaneously controlling the temperature of the electroporation reaction well contents.

Temperature control of the electroporation reaction well contents is performed via a thermally-conductive, temperature controlled surface that mates with the bottom surface of the electroporation array assembly, achieving intimate contact between the two surfaces via a spring loaded mechanism. The electroporation reaction volumes are reduced to a lower temperature (~4° C.), reducing the effects of Joule heating during the electroporation step, and preventing evaporation of the microliter reaction volumes during the loading step. Heating may be performed in an automated and rapid fashion, bringing the temperature to ~37° C. during the recovery and outgrowth periods. Advantageously, this negates the need for ice baths, and reduces the time it takes to reach appropriate recovery temperature, increasing overall transformation efficiency by increased cell viability.

The open face configuration, with electrodes at the bottom of the reaction well leaves the sample volume exposed and openly accessible. The additional volume above the sample can be filled with recovery buffer immediately following electroporation, enabling the user to perform electroporation, the subsequent 'recovery period,' and cell outgrowth in the same device. Advantageously, this decreases the amount of experimental steps, consumable waste, and increases the overall process efficiency.

II. Electroporation Devices and Systems

Figure 1B:
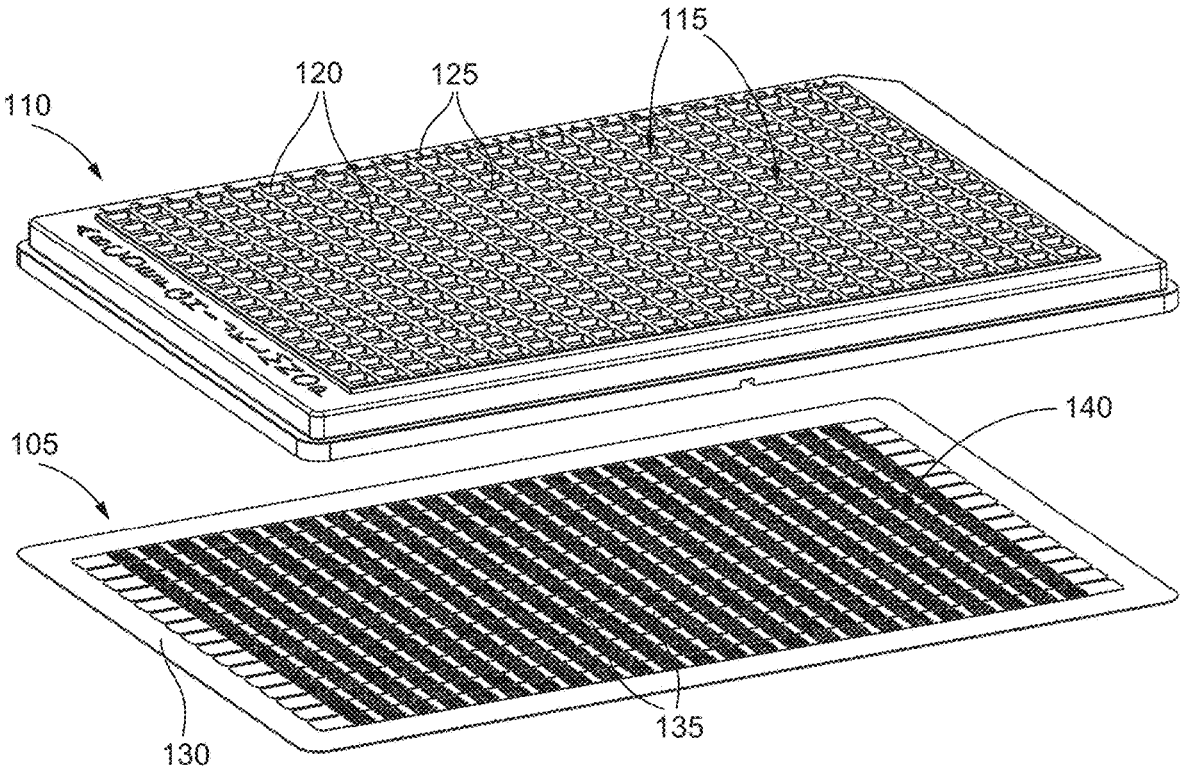
Figure 1C:
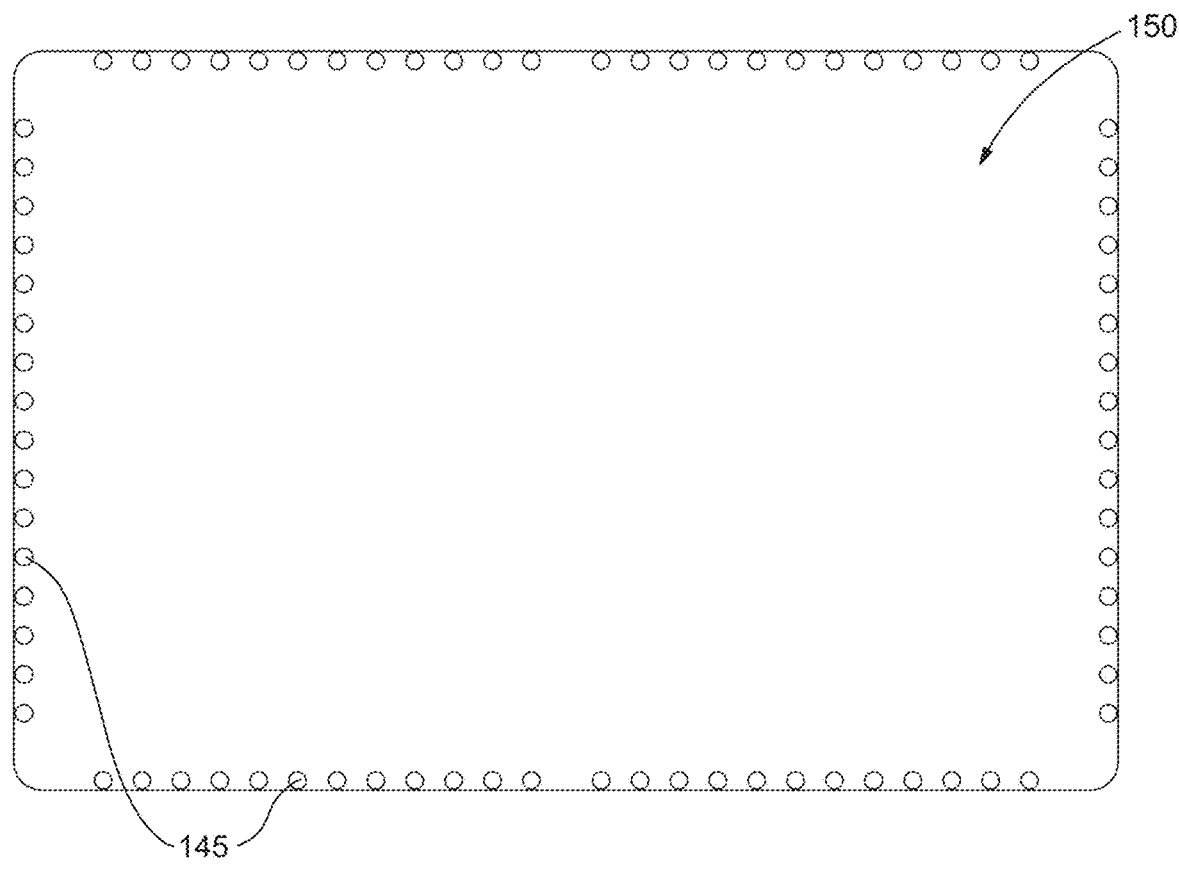

FIGS. 1A-1G show an electroporation array assembly 100 in accordance with various embodiments. FIG. 1A shows an assembled view of an electroporation array assembly 100 and FIG. 1B shows an exploded view of the electroporation array assembly 100. The electroporation array assembly 100 comprises two layers: (i) the electrode array layer 105, and (ii) the polymer housing 110 stacked on top of the electrode array layer 105. The polymer housing 110 provides fluidic isolation between reaction wells 115 while maintaining an opening at a top of each reaction well 115 (an opening to an external environment). The open face configuration, with the electrode array layer 105 at the bottom of the reaction wells 115 leaves the sample volume exposed and openly accessible. Although the electroporation array assembly 100 is illustrated and described with respect to an array, it should be understood that the device could be designed as a single reaction chamber/well device. The electrode array layer 105 may be thin ranging from 100 to 3000 µm; whereas the polymer housing 110 may be relatively thicker ranging from 500 to 6000 When assembled, the electrode array layer 105 is bonded to the polymer housing 110. In some instances, the bonding is a hermetic bond such that the interface between the electrode array layer 105 and polymer housing 110 airtight (preventing the passage of air, oxygen, or other gases). In other instances, the bonding is a seal such that the interface between the electrode array layer 105 and polymer housing 110 liquid tight (preventing the passage of liquid molecules).

The polymer housing 110 contains an array of through hole vacancies 120 that make up the side walls 125 of the reaction wells 115, providing fluidic isolation and structural rigidity. The polymer housing 110 may be made of any biocompatible (i.e., biologically inert) polymer material including, for example, PMMA [poly(methylmethacrylate)]-VSUVT or Zeonor 1060R. The total width of the reaction wells 115 can range from 1 to 20 mm, with the depth ranging from 1 to 50 mm, depending on design of the electroporation array assembly 100. In some instances, the polymer housing is hydrophobic. In some instances, the reaction wells 115 undergo a process to modify the side walls 125 and make the side walls 125 hydrophobic with a water contact angle of greater than 60 degrees measured using a goniometer. In certain instances, the side walls 125 of the reaction wells 115 are processed to be above average hydrophobic with a water contact angle of greater than 80 degrees or superhydrophobic with a contact angle of greater than 150 degrees. The process may be a (i) chemical etching, (ii) solution immersion, (iii) laser electrodeposition, (iv) template deposition, (v) spray coating, or (vi) any combination thereof. The above average hydrophobic or superhydrophobic processing ensures that any sample deposited into the reaction wells 115 is completely disposed on the bottom floor area or surface of the reaction wells 115 (i.e., no minute trace of sample from the depositing process remains on the side walls 125).

The electrode array layer 105 comprises a substrate 130 supporting multiple electroporation electrodes 135. The substrate 130 is formed of a dielectric material such as a polymer having suitable dielectric (i.e., electrically insulating), flexibility and biocompatibility characteristics. Polyurethane, polycarbonate, silicone, polyethylene, fluoropolymer and/or other medical polymers, copolymers and combinations or blends may be used. The electroporation electrodes 135 (described hereafter simply as "electrodes") are configured to apply an external electric field to a sample (e.g., a biological sample) in each of the reaction wells 115 (with respect to cells the application of the field results in an increase in electric conductivity and permeability of the cell plasma membrane).

The top surface 140 of the electrode array layer 105 makes up the bottom floor area or surface of the reaction wells 115, with electrodes 135 partially or completely covering the entirety of the bottom of each reaction well 115. An electrical connection is routed from the electrodes 135 through the substrate 130 to contacts 145 (i.e., electrically conductive elements, pins, wires, tabs, pads, etc.) on the bottom surface 150 of the electrode array layer 105, which are used to interface with the control unit (see, FIG. 1C which shows the bottom side of the electroporation array assembly 100). The conductive material selected for the contacts 145 should have good electrical conductivity and may include pure metals, metal alloys, combinations of metals and dielectrics, and the like. For example, the conductive material may be platinum (Pt), platinum/iridium (Pt/Ir), titanium (Ti), gold (Au), gold/titanium (Au/Ti), or any alloy thereof. The contacts 145 on the bottom surface 150 of the electrode array layer 105 may be positioned on the periphery of the electrode array layer 105, so that the center area of the bottom surface 150 is physically uninhibited and available for thermal contact, allowing the corresponding control unit to provide electronic connectivity to the electrodes 135 while simultaneously controlling the temperature of the sample in the reaction wells 115.

Figure 1D:
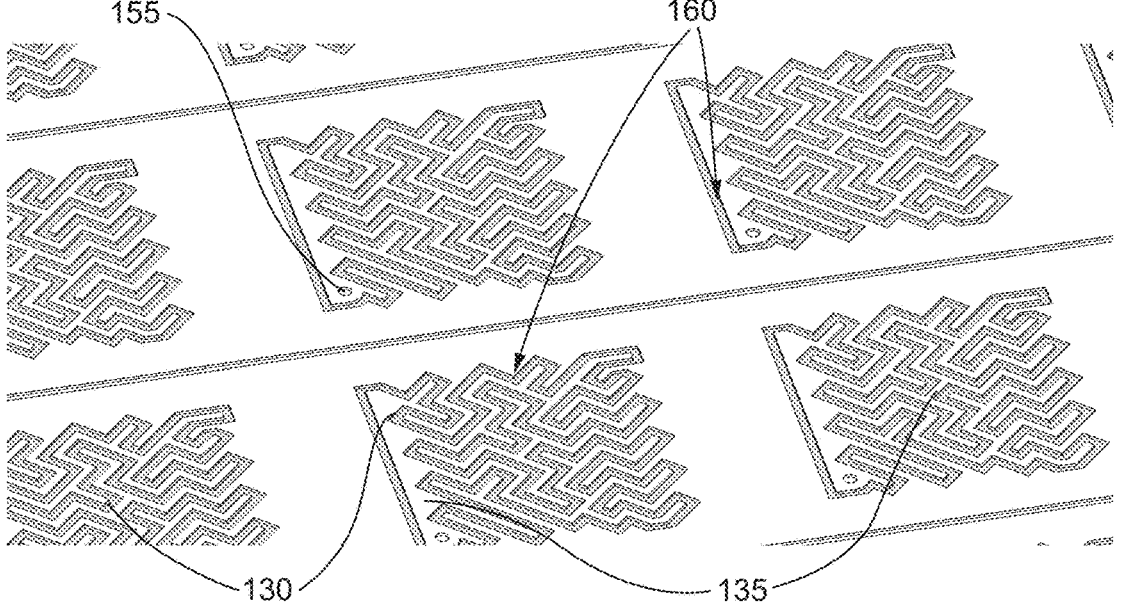
Figures 1E, 1F:
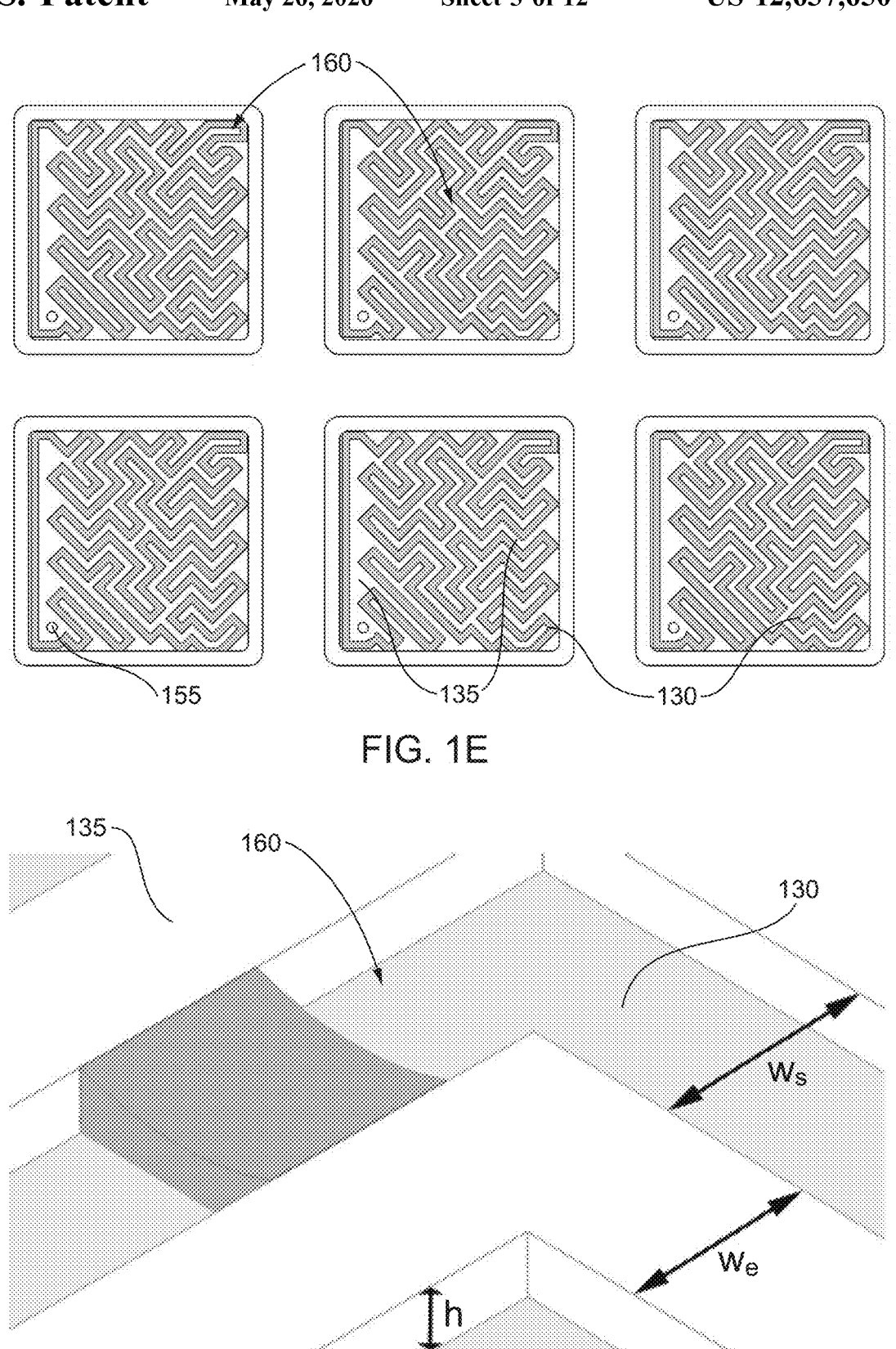

FIG. 1D shows the electrodes 135 arranged on the top surface 140 of the electrode array layer 105, and FIG. 1E shows a close up view into the reaction wells 115 of the electroporation array assembly 100, showing the electrodes 135 at the bottom floor area. The electrodes 135 are formed on a top surface of the substrate 130 in electrical connection with a wiring layer that is within the substrate 130. The wiring layer passes through via holes 155 in the substrate 130 to the contacts 145. The electrodes 135 and wiring layer are fabricated from one or more conductive traces using various shapes and patterns. The conductive traces are comprised of one or more layers of conductive material. The conductive material selected for the one or more conductive traces should have good electrical conductivity and may include pure metals, metal alloys, combinations of metals and dielectrics, and the like. For example, the conductive material may be platinum (Pt), platinum/iridium (Pt/Ir), titanium (Ti), gold (Au), gold/titanium (Au/Ti), or any alloy thereof. In some embodiments, it is also desirable that the conductive material selected for the one or more conductive traces have thermal expansion characteristics or a coefficient of thermal expansion (CTE) that is approximately equal to that of CTE of the substrate 130. Matching the CTE of components that contact one another is desirable because it eliminates the development of thermal stresses, which may occur during fabrication and the operation of the electroporation array assembly 100, and thus eliminates a known cause of mechanical failure in the components. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

In some instances, each reaction well contains a pair of electrodes 135. Each pair of electrodes 135 comprises a ground electrode adjacent to a corresponding active electrode capable of receiving an applied voltage. The pair of electrodes 135 may be coplanar with a interdigitated configuration or geometry (an interlocking of the pair of electrodes 135 with fingerlike projections). In certain instances, the interdigitated configuration or geometry is omnidirectional (fingerlike projections in all directions). In other instances, the interdigitated configuration or geometry is unidirectional or multidirectional (fingerlike projections in one or more directions). In some instances, the electrodes 135 are planar or substantially planar with the substrate 130. In other instances, the electrodes 135 protrude up or are raised from the substrate 130. As shown in FIG. 1D, the electrodes 135 (shown in white) protrude up or are raised from the substrate 130 (shown in grey), with protrusion heights ranging from 10 to 2000 The gap spacing between electrodes 135 and width of the conductive traces range from 1 to 500 with the height of the electrodes 135 in the range from 20 to 100 $\mu$m, depending on design of the electroporation array assembly. The protrusion and gap spacing of the electrodes 135 creates a series of adjacent open faced microchannels 160 for the sample to flow through. FIG. 1F illustrates a minimum sample volume required to undergo electroporation; with electrode dimensions height h, width $w_e$, and spacing $w_s$, the approximate minimum volume needed is: $h \times (w_s)^2$.

The top surface 140 of the electrode array layer 105 undergoes a process prior to bonding with the polymer housing, to modify the top surface 140 of the electrode array layer 105 and make it hydrophilic with a water contact angle of less than 45 degrees measured using a goniometer. In certain instances, the top surface 140 of the electrode array layer 105 is processed to be extremely hydrophilic with a water contact angle of less than 40 degrees or superhydrophilic with a contact angle of less than 20 degrees. The process may be a (i) plasma irradiation, (ii) chemical vapor deposition, (iii) ultraviolet irradiation, (iv) etching, or (v) any combination thereof. In some instances, the process is selective such that only the substrate 130 or only the electrodes 135 are modified to make them hydrophilic. In other instances, the process is applicable across material such that both the substrate 130 and the electrodes 135 are modified to make them hydrophilic. The hydrophilic processing increases the surface area contact of the sample with the electrodes, therefore increasing the permeation of the electric field emanating from the electrodes through the sample and increasing the sensitivity of impedance spectroscopy signals collected by the electrodes. Further, the hydrophilic processing increases the volume fraction of the sample that experiences the minimum required electric field strength required to perform successful electroporation or transport of the desired biological particle(s) into cells of the sample. Consequently, the hydrophilic processing increases the number of cells that successfully uptake the desired biological particles, increasing the transformation efficiency when compared to an analogous electroporation electrode configuration that has not undergone the hydrophilic processing.

Figure 1G:
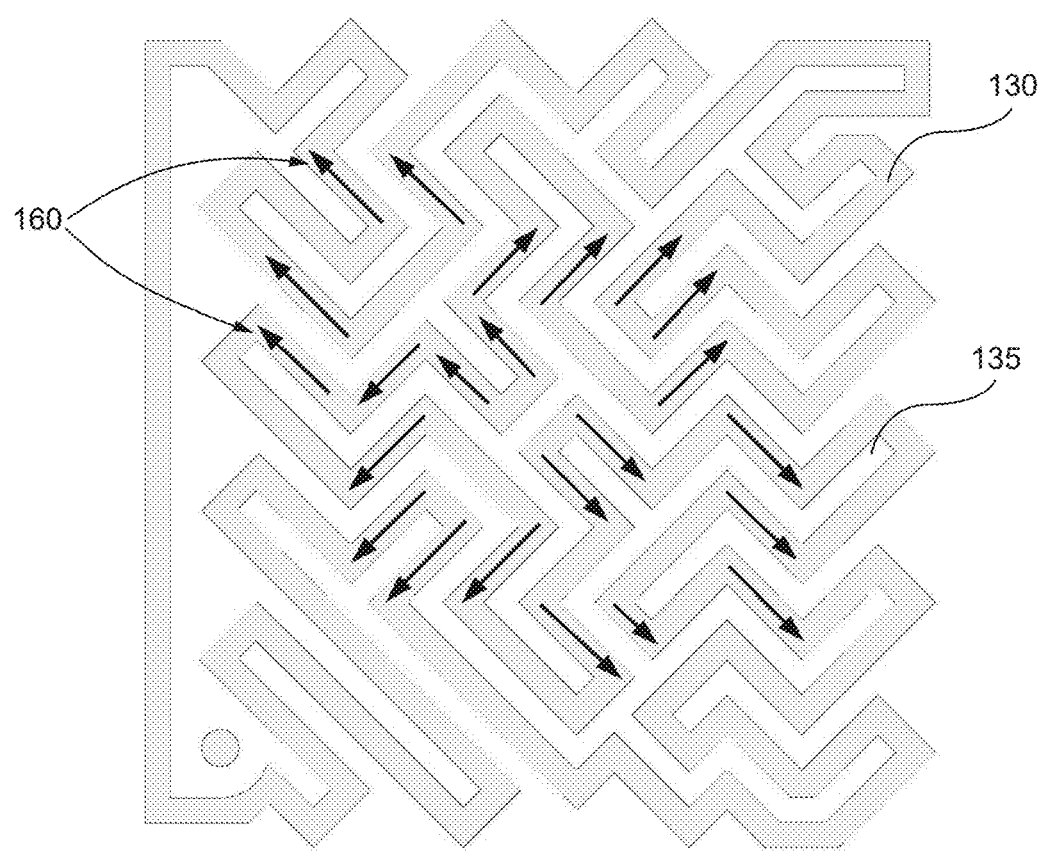

As shown in FIG. 1G, the 2D top down design of the electrodes 135 are arranged in a manner to utilize capillary forces (denoted by the black arrows) afforded by the 3D structure (i.e., microchannels 160) and hydrophilic treatment of the top surface 140 of the electrode array layer 105, to pull the dispensed aqueous reaction volume from the center of the reaction well floor, spreading it out over the entire surface of the electrodes 135. In certain instances, the interdigitated configuration or geometry of the electrodes 135 creates omnidirectional microchannels 160 to assist with pulling the dispensed aqueous reaction volume from the center of the reaction well floor, spreading it out over the entire surface of the electrodes 135. In other instances, the interdigitated configuration or geometry of the electrodes 135 creates unidirectional or multidirectional microchannels 160 (microchannels in one or more directions) to assist with pulling the dispensed aqueous reaction volume from the center of the reaction well floor, spreading it out over the entire surface of the electrodes 135. This maximizes the contact of the sample with the surface of the electrodes 135, allowing for a much higher percentage of the reaction volume to experience the relevant strength of the applied electric field required to perform electroporation. This configuration may be used for reduced reaction volumes ranging from 0.1 nL to 10 µL. The additional volume above the sample can be filled with recovery buffer immediately following electroporation, enabling the user to perform electroporation, the subsequent 'recovery period,' and cell outgrowth in the same device.

Figure 2A:
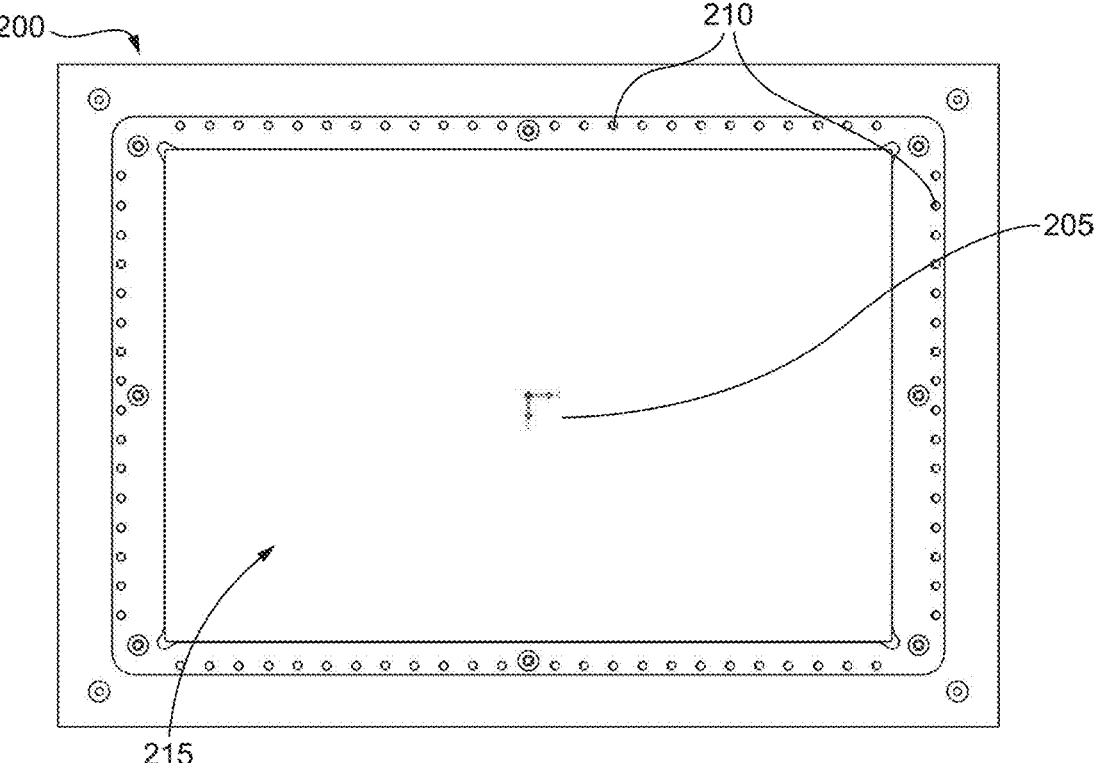
FIGS. 2A-2D show a control unit in accordance with various embodiments.
Figure 2B:
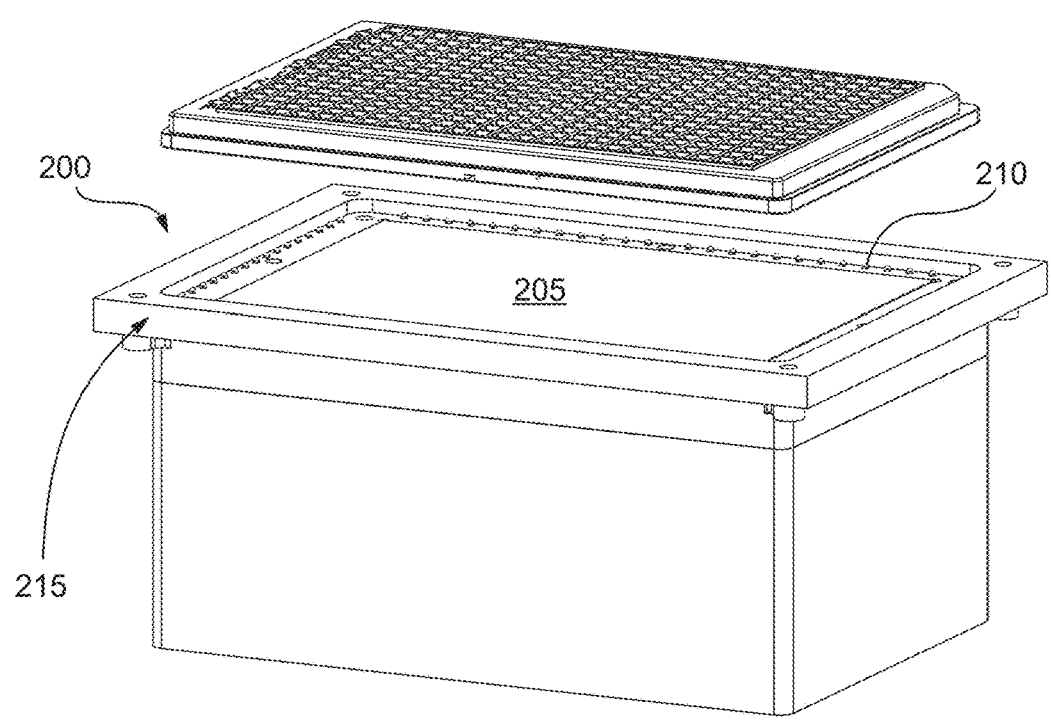
Figure 2C:
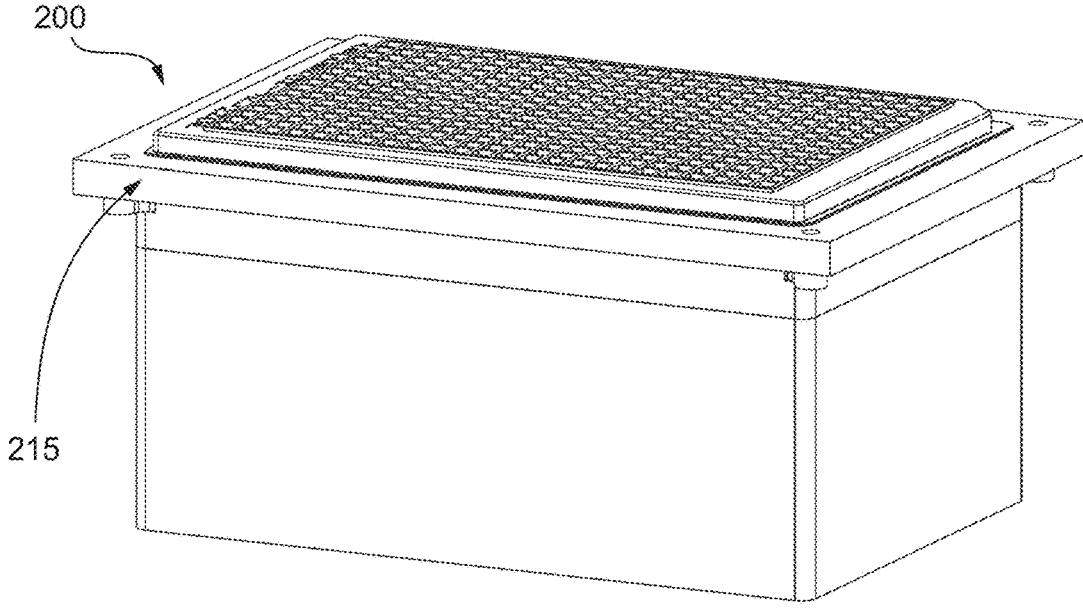

FIGS. 2A-2D show the control unit 200 in accordance with various embodiments. FIGS. 2A-2D illustrate how the control unit 200 interfaces with an the electroporation array assembly (e.g., the electroporation array assembly 100 described with respect to FIGS. 1A-1G) to provide systematic and automated electrical connectivity to the electrodes from the waveform generator, while simultaneously providing temperature control of the electroporation reaction volume(s), with the capability of a mixing mechanism for the post electroporation recovery and incubation of the biological cells. FIG. 2A is a top down view of the control unit 200, showing the control unit's temperature controlled pad 205 surrounded by contacts 210 (i.e., electrically conductive elements, pins (e.g., spring loaded pogo pins), wires, tabs, pads, etc.). The conductive material selected for the contacts 210 should have good electrical conductivity and may include pure metals, metal alloys, combinations of metals and dielectrics, and the like. For example, the conductive material may be platinum (Pt), platinum/iridium (Pt/Ir), titanium (Ti), gold (Au), gold/titanium (Au/Ti), or any alloy thereof. FIG. 2C shows the electroporation array assembly laid down onto the top surface 215 of the control unit 200.

As shown in FIG. 2B, the contacts 210 are arranged on the top surface 215 of the control unit 200 to align with and make electrical contact with the contacts on the bottom surface of the electroporation array assembly (e.g., the contacts 145 described with respect to FIG. 1). The control unit further comprises an agitator (not shown but included within base of control unit 200) for controlling shaking or stirring of the sample in the electroporation array assembly. In some instances, the agitator is contactless such as an oscillating agitator or a vibrating agitator that causes the electroporation array assembly to shake or vibrate, which indirectly shakes or stirs the sample in the reaction wells.

Figure 2D:
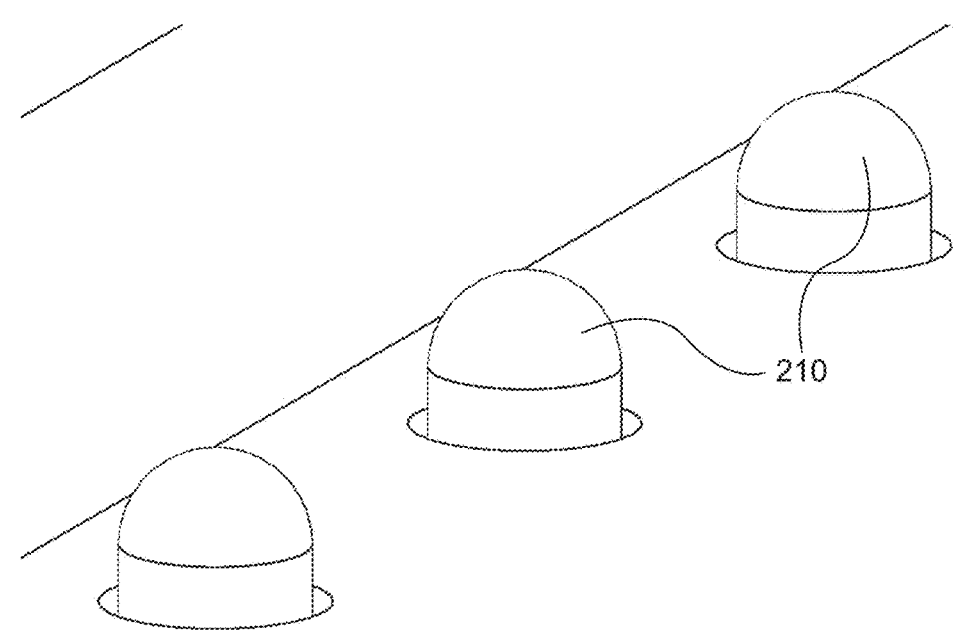

The contacts 210 on the top surface 215 of control unit 200 may be positioned on the periphery of the temperature controlled pad 205, so that the center area of the temperature controlled pad 205 is physically uninhibited and available for thermal contact, allowing the control unit 200 to provide electronic connectivity to the electrodes while simultaneously controlling the temperature of contents (e.g., a biological sample) of the reaction wells. Temperature control of the reaction well contents is performed via the thermally-conductive, temperature controlled pad 205 that mates directly with the bottom surface of the electroporation array assembly, achieving intimate contact between the two surfaces and enabling heat energy to be transported through the electrode array layer, to and from the reaction volume of the reaction wells. In some instances as shown in FIG. 2D, the contacts 210 are spring loaded or adjustable in the vertical direction to assist with the temperature controlled pad 205 mating directly with the bottom surface of the electroporation array assembly. The electroporation reaction volumes may be reduced by the temperature controlled pad 205 to a lower temperature (~4° C.), reducing the effects of Joule heating during the electroporation step, and preventing evaporation of the microliter reaction volumes during the loading step. Heating may be performed in an automated and rapid fashion with the temperature controlled pad 205, bringing the temperature to ~37° C. during the recovery and outgrowth periods.

Figure 3:
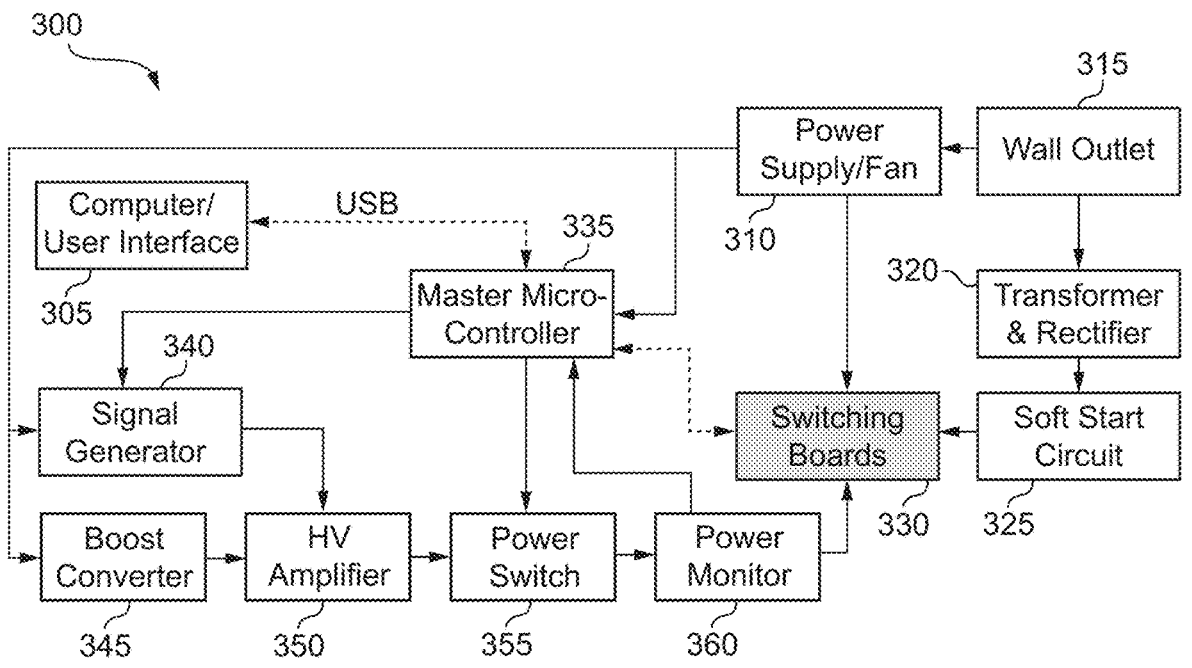
FIG. 3 shows circuit overview of a master board in accordance with various embodiments.

FIG. 3 shows a circuit overview of a master board 300 of a control unit (e.g., the control unit 200 described with respect to FIGS. 2A-2D) for controlling operations of the control unit. The master board 300 comprises a computer/user interface circuit 305, a power supply module 310, a wall outlet 315, a transformer and rectifier 320, a soft start circuit 325, switching boards 330, a master microcontroller 335, a signal generator 340, a boost converter 345, a high voltage amplifier 350, a power switch 355, and a power monitor 360. The computer/user interface circuit 305 communicates with the master microcontroller 335 to control internal and external circuits or devices. For example, the computer/user interface circuit 305 may be used to process signals from sensors or switches as input information or to control displays, and then provide new commands for updating relay or actuator states for output control. The power supply module 310 provides power for the low voltage master board 300 components to carry out its function, e.g., communication, sensing, signal conditioning, etc. The transformer and rectifier 320 provide the voltage levels required for high voltage switching and electroporation. The transformer and rectifier 320 changes both the voltage and the current of an alternating current (AC) power source (e.g., the wall outlet 315) and turn the AC into direct current (DC). The soft start circuit 325 gradually increases the startup current from zero to the final value and allows the output voltage to rise at a slower rate, resulting to a lower peak current during startup. The switching boards 330 comprise multiple switches (e.g., multiplexers) for controlling circuits to each electrode pair by either completing or breaking the circuits. The switching boards 330 are in electrical connection with each electrode and/or electrode pair via the mated contacts of the control unit and electroporation array assembly.

The master microcontroller 335 is an integrated circuit designed to govern a specific operation in an embedded system (e.g., an application-specific integrated circuit (ASIC). The master microcontroller 335 includes a processor, memory and input/output (I/O) peripherals. The signal generator 340 may be internal or external to the control unit and is used to create electronic signals (e.g., repeating or non-repeating voltage waveforms). The signal generator 340 allows for implementation of parametric experimental matrix to be executed, varying a wide range of voltage waveform parameters in order to determine optimal conditions for electroporation for a specific biological cell type and to-be-transformed particle grouping. The voltage waveforms are sent to the electrode pairs through the electrical connection provided by the control unit, from the signal generator 340 in order to power the electrodes and generate the electric field. The boost converter 345 is a DC-to-DC power converter that steps up voltage (while stepping down current) from its input (supply) to its output (load). The high voltage amplifier 350 is used to amplify the input signal to a high voltage output. The power switch 355 is used to control the flow of electricity from the signal generator 340, the boost converter 345, and the high voltage amplifier 350 to the electrode pairs of the electroporation array assembly. The power monitor 360 monitors the high voltage output from the high voltage amplifier 350 to provide feedback to the microcontroller 335 and/or the signal generator 340 for controlling the voltage waveforms being sent to the electrode pairs of the electroporation array assembly.

Figure 4:
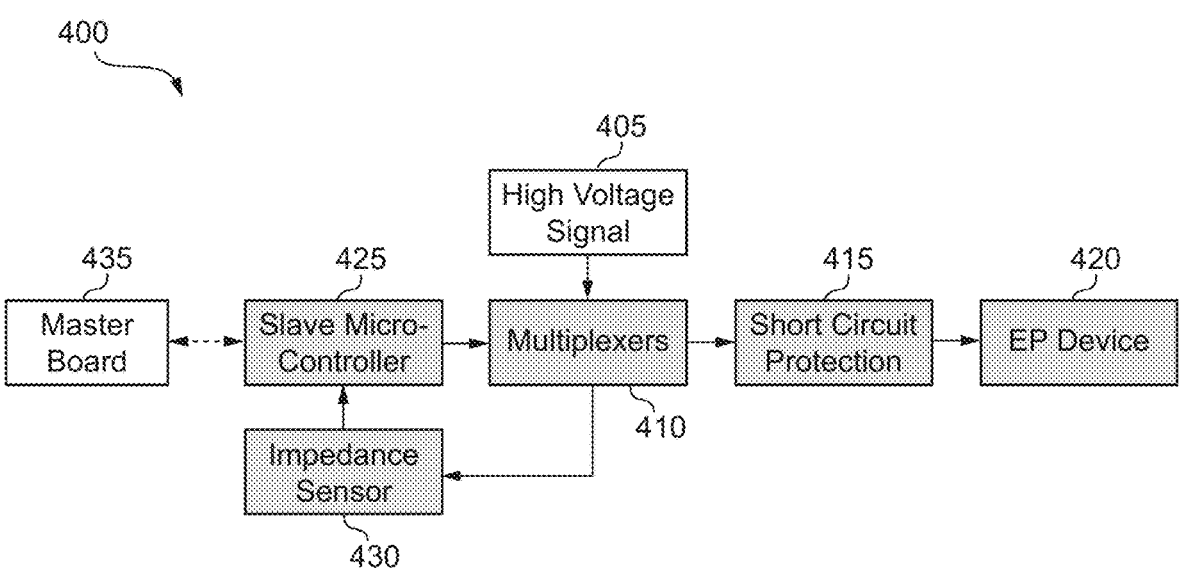
FIG. 4 shows a circuit overview of a switching board in accordance with various embodiments.

FIG. 4 shows a circuit overview of switching boards 400 (e.g., switching boards 330 described with respect to FIG. 3) or controlling circuits to each electrode pair of the electroporation array assembly by either completing or breaking the circuits. The switching boards 400 comprise a high voltage signal 405, multiplexers 410, a short circuit protection 415, an electroporation (EP) device 420, a slave microcontroller 425, an impedance sensor 430, and a master microcontroller connection 435. The high voltage signal 405 comes from the signal generator 340, the boost converter 345, and the high voltage amplifier 350 described with respect to FIG. 3. The master microcontroller connection 435 is with the master microcontroller 335 described with respect to FIG. 3. The multiplexers 410, also known as a data selector or a multiple-input, single-output switch, selects between several analog or digital input signals and forwards the selected input to a single output line. The selection is directed by a separate set of digital inputs known as select lines. The short circuit protection 415 is circuit protection against excessive currents or current beyond the acceptable current rating of the control unit and/or the electroporation array assembly and it operates instantly. As soon as an overcurrent is detected, the short circuit protection 415 trips and breaks the circuit. The electroporation device 420 is comprised of electroporation sites. The slave microcontroller 425 controls the multiplexers 410 in accordance with signals received from the master microcontroller connection 435. The impedance sensor 430 monitors the impedance of circuits connected to the multiplexers 410 to provide pre electroporation feedback for electroporation pulse conditioning and post electroporation feedback for cell monitoring.

Figure 5A:
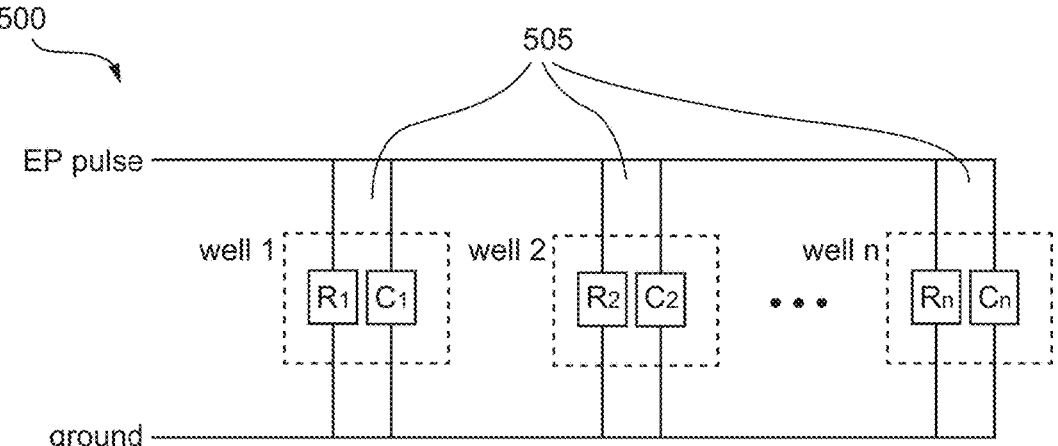
FIG. 5A shows a conventional bridged circuit architecture for an electrode array.

The circuit architecture of the electroporation array assembly enables the electrodes to be individually addressable, allowing different voltage waveforms to be selectively applied to each reaction well individually. FIG. 5A shows the conventional circuit architecture of an electrode array 500. The conventional circuit architecture includes bridged connections 505. A bridge circuit is a topology of electrical circuitry in which two circuit branches (usually in parallel with each other) are "bridged" by a third branch connected between the first two branches at some intermediate point along them. However, in a bridged circuit if one of the pairs of electrodes experiences a short (e.g., sparking or shorting of ground and active electrodes) then all bridged circuits will also short to ground. Thus, if one electrode pair experiences a short, all electrode pairs will no longer function.

Figure 5B:
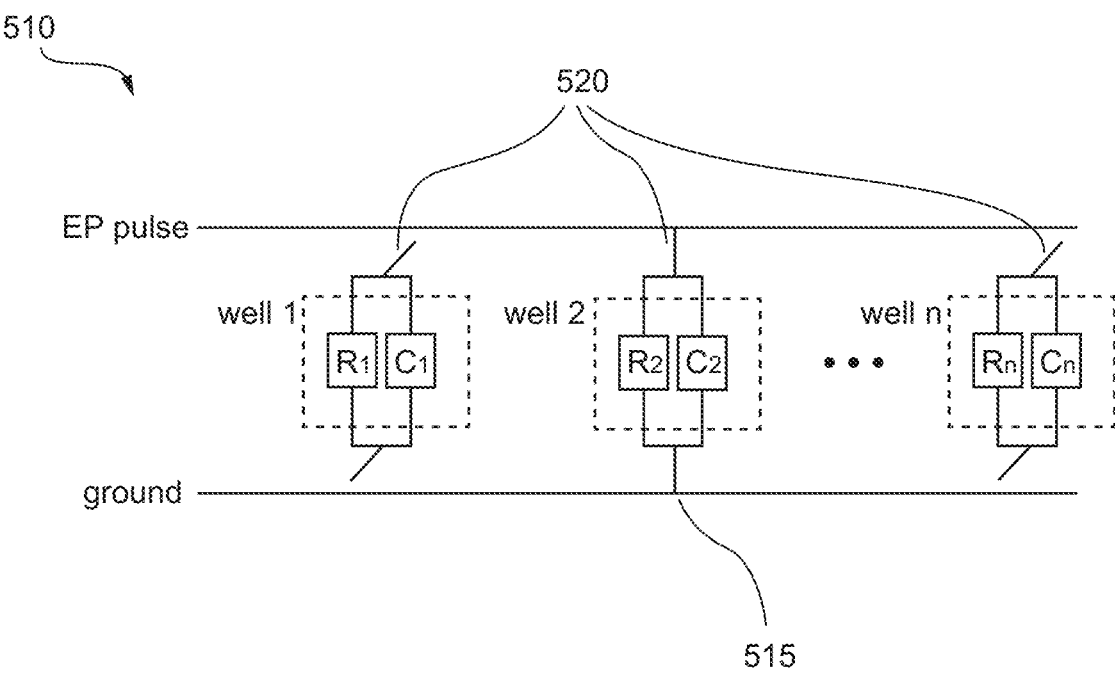
FIG. 5B shows a individually addressable circuit architecture for an electrode array in accordance with various embodiments.

To overcome this problem, the electrode array of the present embodiments enables the electrodes to be individually addressable. FIG. 5B shows the circuit architecture of an electrode array 510 in accordance with various embodiments. The circuit architecture includes isolated connections using either multiple addressable signal lines 515 and/or signal lines with switches 520 that enable each pair of electrodes to be individually addressable. This allows for electroporation experiments to be performed in a single device at large scales, without reduction in electrical resistance resultant of many resistors in parallel if the electroporation electrodes were bridged in parallel. Further, this circuit architecture eliminates the need to vary the applied voltage waveform in order to accommodate the varied resistance resulting from the number of reaction wells occupied. Further, this circuit architecture eliminates the need to vary the applied voltage waveform in order to accommodate the varied resistance resulting from reaction chambers with varied salt concentrations across the array, allowing the user to collect data on the resultant waveform passing through each well individually. Lastly, this circuit architecture preserves experimental viability in the event of a failure in one reaction well, such as sparking or shorting of ground and active electrodes, leaving all other wells unaffected.

Figure 6A:
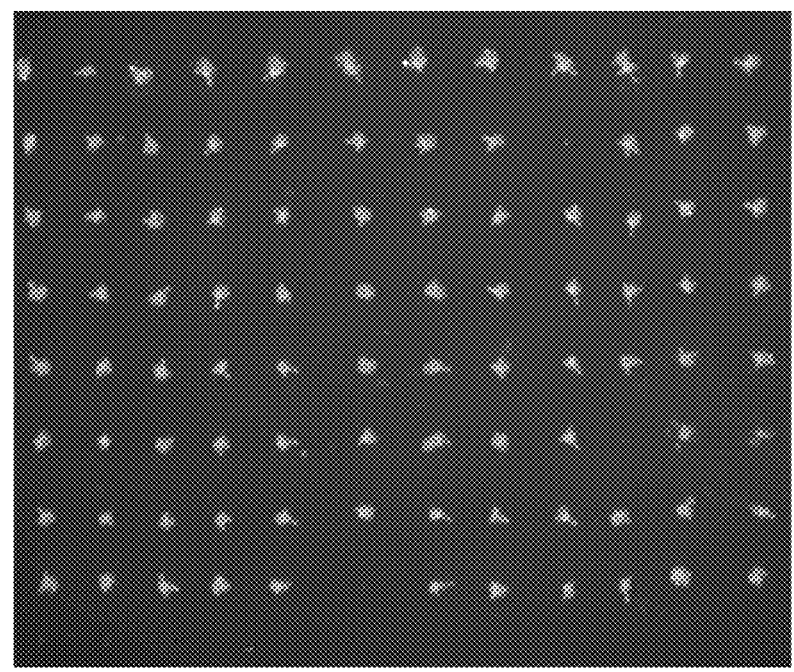
FIGS. 6A and 6B show functionality of an electroporation array assembly in accordance with various embodiments.
Figure 6B:
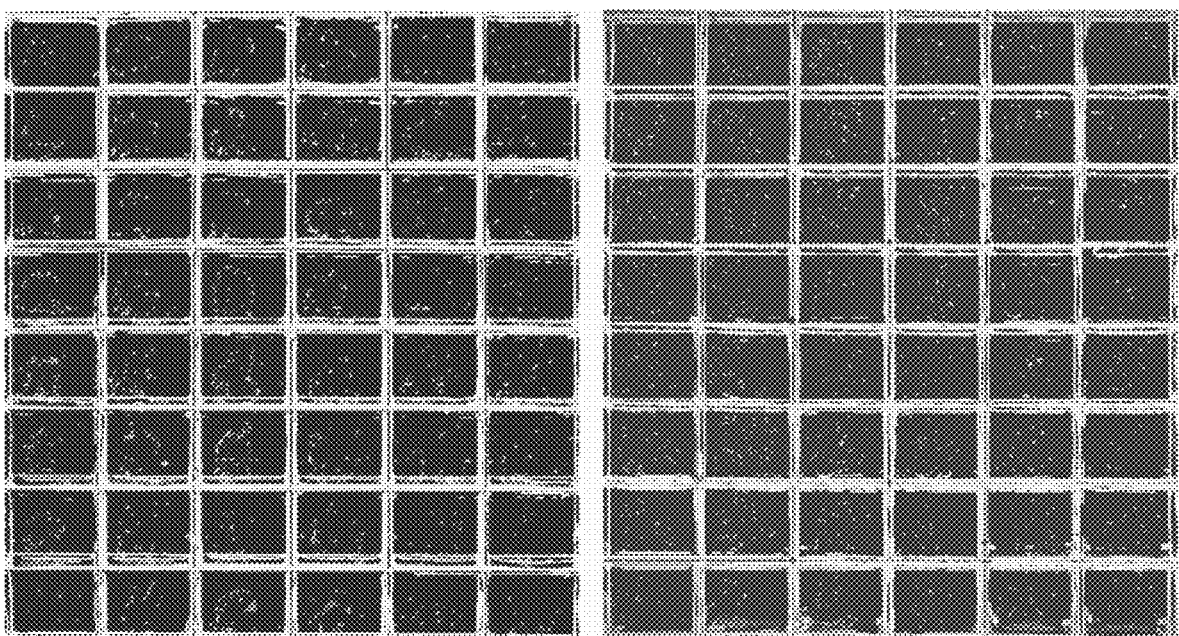

FIGS. 6A-6F illustrate operational capability of the electroporation array assembly. FIG. 6A shows a ninety-six reaction well electroporation array assembly with fluorescence demonstrating uptake of external substances such as chemicals, drugs, or DNA by cells. FIG. 6B show a forty-eight reaction well electroporation array assemblies with fluorescence demonstrating uptake of external substances such as chemicals, drugs, or DNA by cells.

Figure 6C:
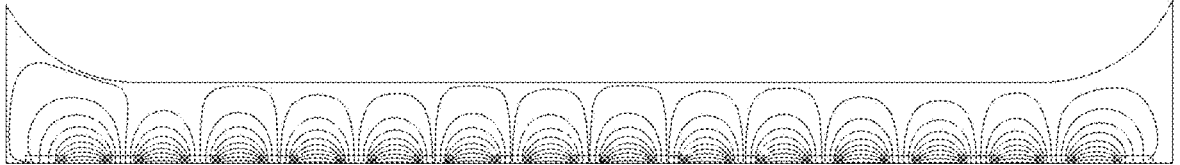
FIGS. 6C and 6D show the electric field propagation through the reaction volume of an electroporation array assembly in accordance with various embodiments.
Figure 6D:
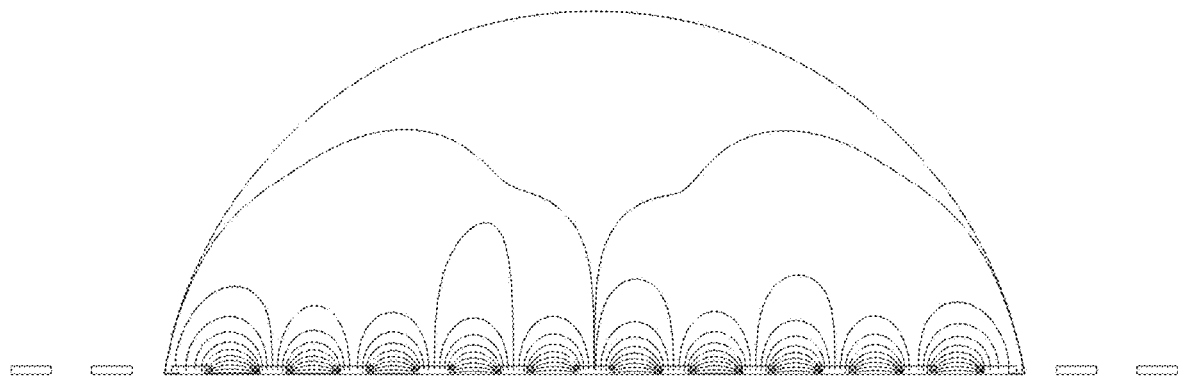

FIGS. 6C and 6D illustrates the electric field propagation through the reaction volume, with density of field lines correlated with electric field strength, under two different conditions. FIG. 6C shows reaction volume has fully wetted the surface of the electrode, afforded by the hydrophilic treatment of the bottom surface of the reaction well in accordance with the various embodiments described herein (i.e., extremely hydrophilic with a contact angle of less than 40 degrees). As shown, the field lines remain tightly spaced throughout the entire volume, meaning that a larger volume fraction experiences more of the full electric field strength required for electroporation. Alternatively, FIG. 6D shows a bottom surface of a reaction chamber with moderate to low hydrophilicity (i.e., a contact angle of between 40 and 60 degrees), thus the reaction volume forms a droplet with a high contact angle, and field line spacing has increased by orders of magnitude for the bulk of the volume.

Figure 6E:
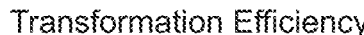
FIGS. 6E and 6F show transformation efficiency of an electroporation array assembly in accordance with various embodiments.
Figure 6E:
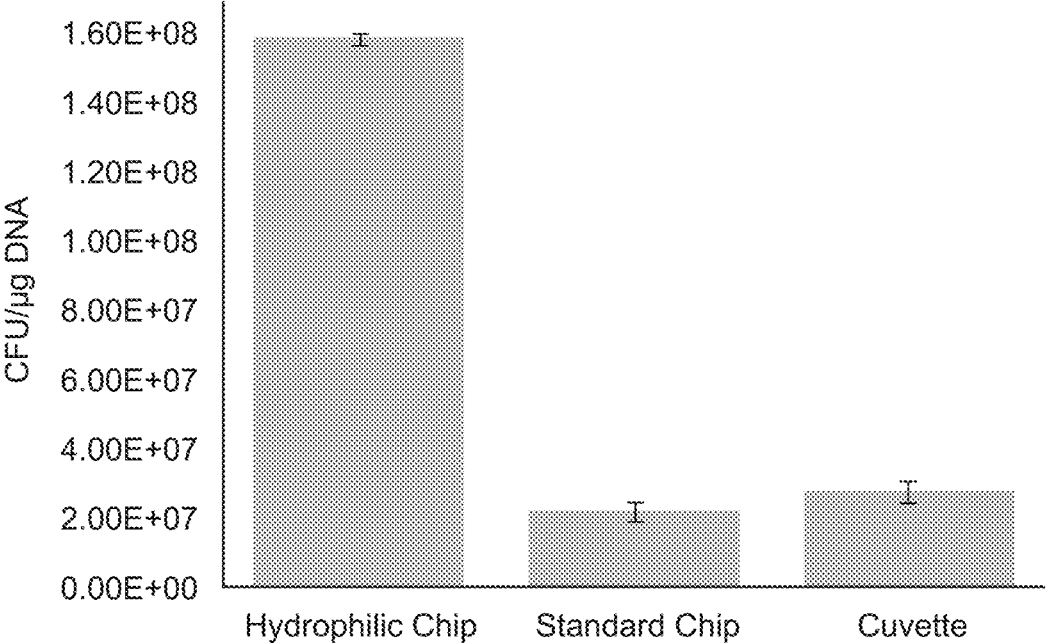
Figure 6F:
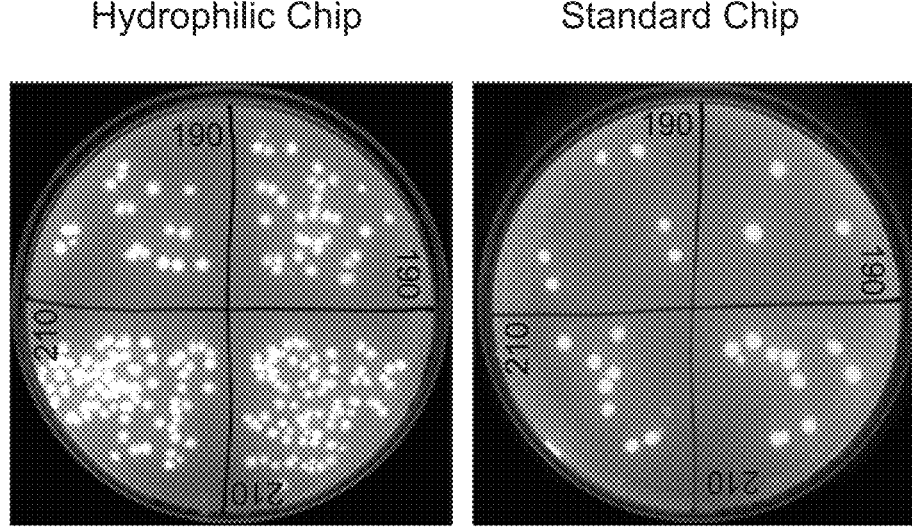

FIGS. 6E and 6F show the improvement in transformation efficiency of an electrode array layer undergone hydrophilic treatment in accordance with the various embodiments described herein (i.e., extremely hydrophilic with a contact angle of less than 40 degrees), compared to one without hydrophilic treatment. For reference, the transformation efficiency of a traditional electroporation cuvette is shown. FIG. 6F shows petri dishes with cell growth and fluorescence demonstrating uptake of external substances such as chemicals, drugs, or DNA by cells using electrode array layer undergone hydrophilic treatment in accordance with the various embodiments described herein versus a standard electrode array layer without hydrophilic treatment.

III. Methods for Electroporation

Figure 7:
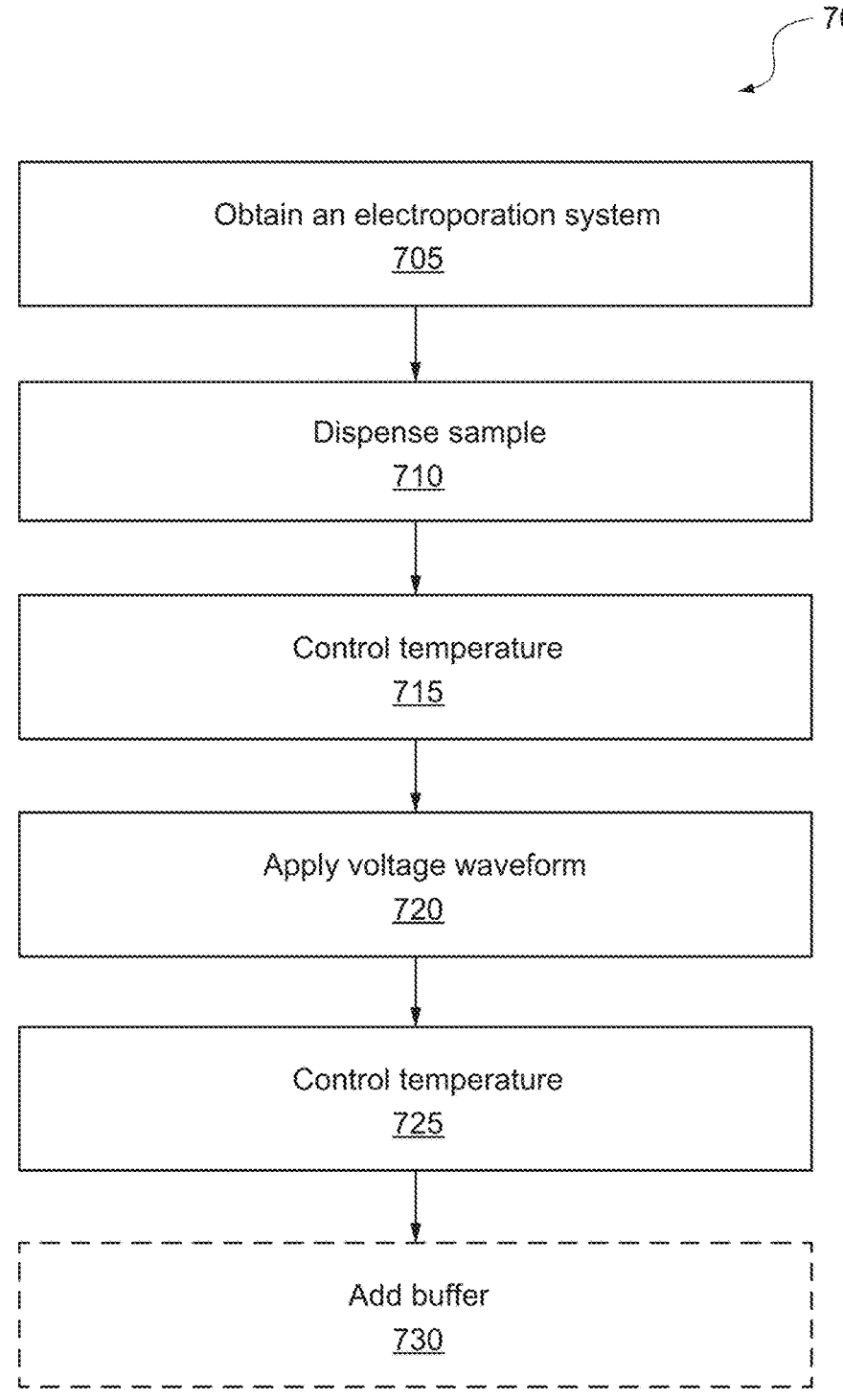
FIG. 7 shows an exemplary flow for electroporation in accordance with various embodiments.

FIG. 7 depicts a simplified flowchart 700 depicting processing performed for electroporation according to embodiments of the present invention. As noted herein, the flowchart of FIG. 7 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

At step 705, a electroporation system (electroporation array assembly and control unit) is provided, obtained, or fabricated in accordance with various aspects discussed herein. At step 710 a sample (e.g., a biological sample) is dispensed into reaction well(s) of the electroporation array assembly. For example, cells may be placed in suspension in an appropriate electroporation buffer and put into the reaction wells of the electroporation array assembly.

At step 715, a temperature of the sample is controlled using the temperature control pad such that the temperature of the sample is at a first temperature or within a first temperature range. For example, the temperature of the sample is reduced or controlled to remove heat energy. In certain instances, the temperature of the sample may be reduce or controlled to maintain a sample temperature of about 4° C. or within a range of 2° C. to 6° C. to reduce effects of joule heating resulting from the applied voltage waveform. The temperature reduction or control may also be used for the purposes of stopping evaporation of small sample volumes, which are normally prone to evaporation at room temperatures, due to a higher surface area to volume ratio. This allows loading of reaction wells at scale (large numbers of reaction wells), by cooling the reagents loaded into the electroporation array chambers, eliminating the risk of evaporation that would occur during the time required to dispense sample in all reaction chambers with reagents.

At step 720, a voltage waveform is applied via circuitry to one or more of the individually addressable electrodes. The applied voltage waveform actuates the individually addressable electrodes and allows for changes in the sample (e.g., increase the permeability of the cell membrane, allowing external substances such as chemicals, drugs, or DNA to be introduced into the cell (also called electrotransfer)).

At step 725, a temperature of the sample is controlled using the temperature control pad such that the temperature of the sample is at a second temperature or within a second temperature range. For example, the temperature of the sample may be increased or controlled to increase heat energy. In some instances, the temperature of the sample may be increased or controlled to maintain a sample temperature of about 37° C. or within a range of 35° C. to 39° C. to increase the survival rate of the biological cells. This allows for cell recovery after electroporation and subsequent cell growth enabling the total automation of the process and negating the need for additional microtiter plates. Moreover, at optional step 730, the additional volume (e.g., 20×) above the sample can be filled with recovery buffer following electroporation, enabling the user to perform electroporation, the subsequent 'recovery period,' and cell outgrowth in the same device. Optionally, during cell recovery and subsequent cell growth, the sample is shaken and mixed using the agitator of the control unit. In some instances, the shaking and mixing are performed in a controlled manner such as scheduled or periodic manner to promote recovery and growth.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:
1. A electroporation array assembly comprising:
a polymer housing forming side walls of reaction wells; and
an electrode array layer bonded to a bottom surface of the polymer housing, wherein:
the electrode array layer forms a bottom surface of the reaction wells,
the electrode array layer comprises: (i) a substrate, and (ii) an array of electrodes formed on the substrate,
the array of electrodes is arranged such that a pair of electrodes is disposed in each of the reaction wells,
each pair of electrodes are coplanar with an interdigitated configuration or geometry,
the substrate, the array of electrodes, or the combination thereof are hydrophilic,
each pair of electrodes comprise a ground electrode adjacent to a corresponding active electrode,
each pair of electrodes protrude from or are raised above a top surface of the substrate, and
microchannels are formed between the ground electrode and the active electrode of each pair of electrodes.

2. The electroporation array assembly of claim 1, wherein the substrate, the array of electrodes, or the combination thereof are hydrophilic with a water contact angle of less than 40 degrees.

3. The electroporation array of claim 1, wherein each electrode of the array of electrodes is comprised of conductive traces, which are formed on the substrate in the interdigitated configuration or geometry.

4. The electroporation array of claim 1, wherein the side walls of the reaction wells are hydrophobic with a water contact angle of greater than 80 degrees.

5. The electroporation array of claim 1, wherein an electrical connection is routed from each pair of electrodes through the substrate to contacts on a bottom surface of the electrode array layer.

6. The electroporation array of claim 5, wherein the electrical connection is a wiring layer comprised of conductive traces and the conductive traces are arranged in a circuit architecture that includes isolated connections using multiple addressable signal lines and/or signal lines with switches that enable each pair of electrodes to be individually addressable.

7. A electroporation system comprising:
an electroporation array assembly comprising:
a housing forming side walls of reaction wells; and
an electrode array layer bonded to a bottom surface of the housing, wherein:
the electrode array layer forms a bottom surface of the reaction wells,
the electrode array layer comprises: (i) a substrate, and (ii) an array of electrodes formed on the substrate,
the substrate, the array of electrodes, or the combination thereof are hydrophilic, and
an electrical connection is routed from each electrode of the array of electrodes through the substrate to a first set of contacts on a bottom surface of the electrode array layer; and
a control unit comprising:
a temperature controlled pad,
a second set of contacts located on the periphery of the temperature controlled pad and arranged to align with and make electrical contact with the first set of contacts of the electroporation array assembly, and
a microcontroller electrically connected to the second set of contacts and configured to deliver a voltage waveform to the array of electrodes via the first set of contacts and the second set of contacts.

8. The electroporation system of claim 7, wherein the temperature controlled pad is in direct contact with the bottom surface of the electrode array layer.

9. The electroporation system of claim 8, wherein the array of electrodes is arranged such that a pair of electrodes is disposed in each of the reaction wells, and each pair of electrodes are coplanar with an interdigitated configuration or geometry.

10. The electroporation system of claim 9, wherein the electrical connection is a wiring layer comprised of conductive traces and the conductive traces are arranged in a circuit architecture that includes isolated connections using either multiple addressable signal lines and/or signal lines with switches that enable each pair of electrodes to be individually addressable.

11. The electroporation system of claim 10, wherein the microcontroller is part of a switching board that further comprises multiplexers configured to individually address each pair of electrodes.

12. The electroporation system of claim 10, wherein:
each pair of electrodes comprise a ground electrode adjacent to a corresponding active electrode,
each pair of electrodes protrude from or are raised above a top surface of the substrate, and
microchannels are formed between the ground electrode and the active electrode of each pair of electrodes.

13. The electroporation system of claim 10, wherein the substrate, the array of electrodes, or the combination thereof are hydrophilic with a water contact angle of less than 40 degrees.

14. The electroporation system of claim 10, wherein each electrode of the array of electrodes is comprised of conductive traces, which are formed on the substrate in the interdigitated configuration or geometry.

15. The electroporation system of claim 7, wherein the side walls of the reaction wells are hydrophobic with a water contact angle of greater than 80 degrees.

16. A method of electroporation comprising:
obtaining a electroporation system comprising: (i) an electroporation array assembly comprising: a housing forming side walls of reaction wells; and an electrode array layer bonded to a bottom surface of the housing, wherein: the electrode array layer forms a bottom surface of the reaction wells, the electrode array layer comprises: (a) a substrate, and (b) an array of electrodes formed on the substrate, the substrate, the array of electrodes, or the combination thereof are hydrophilic, and an electrical connection is routed from each electrode of the array of electrodes through the substrate to a first set of contacts on a bottom surface of the electrode array layer; and (ii) a control unit comprising: a temperature controlled pad, an agitator, a second set of contacts located on the periphery of the temperature controlled pad and arranged to align with and make electrical contact with the first set of contacts of the electroporation array assembly, and a microcontroller electrically connected to the second set of contacts and configured to deliver a voltage waveform to the array of electrodes via the first set of contacts and the second set of contacts;
dispensing a sample into the reactions wells;
controlling, using the temperature control pad, a temperature of the sample such that the temperature of the sample is at a first temperature or within a first temperature range;
applying, using the microcontroller, the voltage waveform to one or more electrodes of the array of electrodes; and
controlling, using the temperature control pad, the temperature of the sample such that the temperature of the sample is at a second temperature or within a second temperature range, wherein the second temperature and the second temperature range are different from the first temperature and the first temperature range.

17. The method of claim 16, wherein the voltage waveform actuates the one or more electrodes and increase permeability of cells in the sample allowing external substances to be introduced into the cells.

18. The method of claim 17, wherein the array of electrodes is arranged such that a pair of electrodes is disposed in each of the reaction wells, and each pair of electrodes are coplanar with a interdigitated configuration or geometry.

19. The method of claim 18, further comprising:
adding a buffer into the reactions wells to facilitate growth of the cells; and agitating, using the agitator of the control unit, the buffer
and sample in the reaction wells.

\* \* \* \* \*